(12) United States Patent
Collis et al.

(10) Patent No.: US 7,687,540 B2
(45) Date of Patent: Mar. 30, 2010

(54) SUBSTITUTED PROPANE PHOSPHINIC ACID ESTERS

(75) Inventors: Alan John Collis, Lexington, MA (US); Gregory Bernard Poli, Bethlehem, PA (US); Yong Mi Choi-Sledeski, Belle Mead, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 203 days.

(21) Appl. No.: 11/775,547

(22) Filed: Jul. 10, 2007

(65) Prior Publication Data

US 2007/0270385 A1 Nov. 22, 2007

Related U.S. Application Data

(63) Continuation of application No. PCT/US2006/004938, filed on Feb. 10, 2006.

(60) Provisional application No. 60/652,152, filed on Feb. 11, 2005.

(51) Int. Cl.
*A61K 31/34* (2006.01)
*C07F 9/28* (2006.01)

(52) U.S. Cl. .................................. 514/469; 549/220

(58) Field of Classification Search ................ 549/220; 514/469

See application file for complete search history.

(56) References Cited

U.S. PATENT DOCUMENTS 5,376,684 A * 12/1994 Mickel ....................... 514/553

OTHER PUBLICATIONS

Froestl, W., et. al., Phosphinic Acid Analogues Of GABA. 2. Selective, Orally Active GABA beta Antagonists, J. Med. Chem. (1995, pp. 3313-3331, vol. 38).

* cited by examiner

*Primary Examiner*—Rei-tsang Shiao
(74) *Attorney, Agent, or Firm*—Balaram Gupta

(57) ABSTRACT

The present invention relates to certain esters of substituted 3-aminopropane phosphinic acid derivatives of formula I:

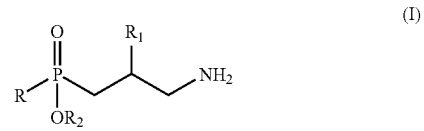

(I)

wherein R, $R_1$ and $R_2$ are as defined herein. The compounds of this invention are useful in treating a variety of diseases including but not limited to depression, anxiety, certain psychiatric symptoms, cognitive impairment and schizophrenia.

13 Claims, No Drawings

SUBSTITUTED PROPANE PHOSPHINIC ACID ESTERS

CROSS REFERENCE TO RELATED APPLICATIONS

This application is a continuation of International application No. PCT/US2006/004,938, filed Feb. 10, 2006, which claims the benefit of U.S. Provisional Application No. 60/652,152, filed Feb. 11, 2005, both of which are incorporated herein by reference in their entirety.

BACKGROUND OF THE INVENTION

1. Field of the Invention

The present invention relates to certain esters of substituted 3-aminopropane phosphinic acid derivatives. More specifically, the present invention relates to esters of 3-amino-2-propane-cycloalkyl(aryl)methyl phosphinic acid derivatives of formula I. This invention also relates to methods of making these compounds. The compounds of this invention are transformed in vivo into biologically active compounds and are, therefore, useful as pharmaceutical agents, especially in the treatment and/or prevention of a variety of diseases including diseases associated with the central nervous system.

2. Description of the Art

U.S. Pat. No. 5,190,933 discloses certain substituted propane phosphinic compounds having therapeutic utility in treating various disorders including cognition and memory disorders, anxiety and depression. However, a problem posed by these compounds is their poor bioabsorption. It has also been reported in the literature that certain compounds such as bisphosphonates exhibit poor absorption from the GI tract. In fact, only one percent of the oral dose is absorbed. As a result, a series of peptidyl prodrugs of these bisphosphonates have been made and shown to improve the drug absorption. See, Ezra, et al., J. Med. Chem. 2000, 43, 3641.

Another concern associated with these structural types of compounds is their oral administration. Generally, such compounds result in patient complaints shortly after dosing; said complaints are usually characterized by the patients as heartburn, esophageal burning, pain and/or difficulty upon swallowing, and/or pain existing behind and/or mid-sternum. It is believed that these complaints originate from esophagitis or esophageal irritation caused by the erosion, ulceration, or other like irritation of the epithelial and mucosal tissues of the upper gastrointestinal tract, generally the mouth through the esophagus, most generally the esophagus.

Another concern with these phosphinic acid compounds is that their slow oral absorption due to high polarity thereby lengthening the time to reach maximum concentration in the plasma. As a consequence, the concentration of the compound is also low in the brain. However, in order to have a faster onset of activity it is necessary that the drug substance level in the brain is high.

It has been reported in the literature that phosphonic acids can be derivatized to form prodrugs, wherein a group that can hydrolyze remotely from the phosphorus oxygen bond (distal hydrolysis) was found to provide better pharmacological profiles including better oral absorption and faster onset of action by having higher levels of the drug substance in the plasma.

All of the references described herein are incorporated herein by reference in their entirety.

Accordingly, it is an object of this invention to provide a series of substituted 3-aminopropane phosphinic acid derivatives which hydrolyze readily under physiological conditions and provide improved pharmacological properties Other objects and further scope of the applicability of the present invention will become apparent from the detailed description that follows.

SUMMARY OF THE INVENTION

Thus in accordance with this invention there is provided a compound, including enantiomers, stereoisomers, and tautomers of said compound and pharmaceutically acceptable salts, solvates or derivatives thereof, with said compound having the general structure shown in formula I:

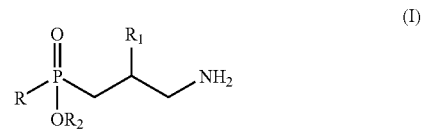

wherein:
R is $C_{1-8}$alkyl, $C_{3-8}$cycloalkyl$C_{1-4}$alkyl, aryl$C_{1-4}$alkyl or fluoroalkyl of the formula $C_nH_xF_y$ wherein n is an integer from 1 to 4, x is an integer from 0 to 8, y is an integer from 1 to 9 and sum of x and y is 2n+1;
$R_1$ is hydrogen or hydroxy;
$R_2$ is substituted or unsubstituted aryl, aryl$C_{1-4}$alkyl, heteroaryl or heteroarylalkyl, or CHWOCOX; wherein
W is hydrogen or $C_{1-4}$alkyl;
X is $C_{1-4}$alkyl, $C_{3-8}$cycloalkyl, aryl, heteroaryl, NHY or OY; and wherein
Y is $C_{1-4}$alkyl, $C_{3-8}$cycloalkyl, aryl or heteroaryl.

The compounds of this invention can be formulated into pharmaceutical compositions and are useful in treating a variety of disease states including but not limited to depression, bipolar disorders, anxiety disorders, psychiatric symptoms, cognitive impairment or memory disorders, schizophrenia, neuropathic pain and fibromyalgia.

DETAILED DESCRIPTION OF THE INVENTION

The terms as used herein have the following meanings:

As used herein, the expression "$C_{1-6}$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-4}$alkoxy", "$C_{1-4}$thioalkyl" "$C_{1-4}$alkoxy$C_{1-4}$alkyl", "hydroxy$C_{1-4}$alkyl", "$C_{1-4}$alkylcarbonyl", "$C_{1-4}$alkoxycarbonyl$C_{1-4}$alkyl", "$C_{1-4}$alkoxycarbonyl", "amino$C_{1-4}$alkyl", "$C_{1-4}$alkylamino", "$C_{1-4}$alkylcarbamoyl$C_{1-6}$alkyl", "$C_{1-4}$dialkylcarbamoyl$C_{1-4}$alkyl" "mono- or di-$C_{1-4}$alkylamino$C_{1-4}$alkyl", "amino$C_{1-4}$alkylcarbonyl" "diphenyl$C_{1-4}$alkyl", "phenyl$C_{1-4}$alkyl", "phenylcarboyl$C_{1-4}$alkyl" and "phenoxy$C_{1-4}$alkyl" are to be construed accordingly.

As used herein, the expression "cycloalkyl" includes all of the known cyclic radicals. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein the expression "$C_{1-4}$acyl" shall have the same meaning as "$C_{1-6}$alkanoyl", which can also be represented structurally as "R—CO—," where R is a $C_{1-3}$alkyl as defined herein. Additionally, "$C_{1-3}$alkylcarbonyl" shall mean same as $C_{1-4}$acyl. Specifically, "$C_{1-4}$acyl" shall mean formyl, acetyl or ethanoyl, propanoyl, n-butanoyl, etc. Derived expressions such as "$C_{1-4}$acyloxy" and "$C_{1-4}$acyloxyalkyl" are to be construed accordingly.

As used herein, the expression "$C_{1-6}$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$ perfluoroalkoxy", is to be construed accordingly.

As used herein, the expression "$C_{6-12}$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "$C_{6-12}$arylsulfonyl," is to be construed accordingly.

As used herein, the expression "$C_{6-12}$aryl$C_{1-4}$alkyl" means that the $C_{6-12}$aryl as defined herein is further attached to $C_{1-4}$alkyl as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Representative 5-memebered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, pyridofuranyl, pyridothienyl, and the like radicals. Other suitable "heteroaryl" for purposes of this invention include oxo-1,3-dihydroisobenzofuranyl, 5-methyl-[1,3]dioxol-2-onemethyl, and the like.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

As used herein, the term "prodrug" shall have the generally accepted meaning in the art. One such definition includes a pharmacologically inactive chemical entity that when metabolized or chemically transformed by a biological system such as a mammalian system is converted into a pharmacologically active substance.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

The term "solvate" as used herein means that an aggregate that consists of a solute ion or molecule with one or more solvent molecules. Similarly, a "hydrate" means that a solute ion or molecule with one or more water molecules.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $C_{2-6}$alkenyl, $C_{1-6}$ perfluoroalkyl, phenyl, hydroxy, —$CO_2H$, an ester, an amide, $C_1$-$C_6$alkoxy, $C_1$-$C_6$thioalkyl, $C_1$-$C_6$ perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The term "treating" refers to:
(i) preventing a disease, disorder or condition from occurring in a patient that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Thus, in accordance with the practice of this invention there is provided a compound, including enantiomers, stereoisomers, and tautomers of said compound and pharmaceutically acceptable salts, solvates or derivatives thereof, with said compound having the general structure shown in formula I:

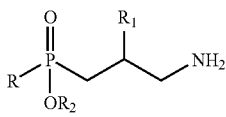

wherein:
R is $C_{1-8}$alkyl, $C_{3-8}$cycloalkyl$C_{1-4}$alkyl, aryl$C_{1-4}$alkyl or fluoroalkyl of the formula $C_nH_xF_y$, wherein n is an integer from 1 to 4, x is an integer from 0 to 8, y is an integer from 1 to 9 and sum of x and y is 2n+1;
$R_1$ is hydrogen or hydroxy;
$R_2$ is substituted or unsubstituted aryl, aryl$C_{1-4}$alkyl, heteroaryl or heteroarylalkyl, or CHWOCOX; wherein
W is hydrogen or $C_{1-4}$alkyl;
X is $C_{1-4}$alkyl, $C_{3-8}$cycloalkyl, aryl, heteroaryl, NHY or OY; and wherein
Y is $C_{1-4}$alkyl, $C_{3-8}$cycloalkyl, aryl or heteroaryl.

In one aspect of this invention the compound of formula (I) having the following substituents are preferred:
R is cyclopropylmethyl, cyclobutylmethyl, cyclopentylmethyl, cyclohexylmethyl, cycloheptylmethyl, cyclohexylethyl, cyclohexylpropyl, benzyl, and phenylethyl;
$R_1$ is hydroxy;
$R_2$ is substituted or unsubstituted phenyl, benzyl or oxo-1, 3-dihydroisobenzofuranyl, 5-methyl-[1,3]dioxol-2-one-methyl, gamma-butyrolacton-4-yl, CHWOCOX; wherein
W is hydrogen, methyl, ethyl, n-propyl or sec-butyl;
X is methyl, ethyl, n-propyl, n-butyl, sec-butyl, tert-butyl, cyclohexyl or OY; and wherein
Y is methyl, ethyl or n-propyl.

In this particular embodiment of the invention, the compound of formula (I), wherein R is $C_{3-8}$cycloalkyl$C_{1-4}$alkyl and $R_1$ is hydroxy is preferred. In another embodiment of this aspect of the invention, the compound of formula (I), wherein R is aryl$C_{1-4}$alkyl and $R_1$ is hydroxy is preferred. In yet another embodiment of this invention, the compound of formula (I), wherein R is $C_{5-7}$cycloalkyl$C_{1-4}$alkyl and $R_1$ is hydroxy is also preferred. Finally, in another embodiment of this invention, the compound of formula (I), wherein R is phenyl$C_{1-4}$alkyl and $R_1$ is hydroxy is preferred.

In one embodiment, the compound of the invention is represented by formula IA:

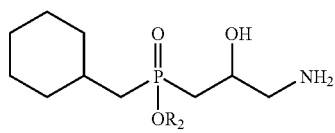

In another embodiment of this invention, the compound of this invention is a stereospecific isomer of formula IB:

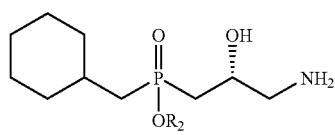

wherein
$R_2$ is substituted or unsubstituted phenyl, benzyl, oxo-1,3-dihydroisobenzofuranyl or 5-methyl-[1,3]dioxol-2-one-methyl, or CHWOCOX; wherein
W is hydrogen, methyl, ethyl, n-propyl or sec-butyl;
X is methyl, ethyl, n-propyl, n-butyl, sec-butyl, tert-butyl, cyclohexyl or OY; and wherein
Y is methyl, ethyl or n-propyl.

As representative examples of compounds of formula I of this invention, without any limitation, the following compounds may be enumerated:
((R)-3-amino-2-hydroxy-propyl)-cyclohexylmethyl-phosphinic acid 3-oxo-1,3-dihydro-isobenzofuran-1-yl ester;
2,2-dimethyl-propionic acid ((R)-3-amino-2-hydroxy-propyl)-cyclohexylmethyl-phosphinoyloxymethyl ester;
((R)-3-amino-2-hydroxy-propyl)-cyclohexylmethyl-phosphinic acid ethoxycarbonyloxymethyl ester;
((R)-3-amino-2-hydroxy-propyl)-cyclohexylmethyl-phosphinic acid phenyl ester;
((R)-3-amino-2-hydroxy-propyl)-cyclohexylmethyl-phosphinic acid benzyl ester;
(3-amino-2-hydroxy-propyl)-cyclohexylmethyl-phosphinic acid 5-methyl-2-oxo-[1,3]dioxol-4-ylmethyl ester; or
a pharmaceutically acceptable salt, hydrate or solvate thereof.

In another preferred embodiment of this invention, the following specific compound within the scope of formula I may be mentioned: 2,2-dimethyl-propionic acid ((R)-3-amino-2-hydroxy-propyl)-cyclohexylmethyl-phosphinoyloxymethyl ester or a pharmaceutically acceptable salt, hydrate or solvate thereof.

In another preferred embodiment of this invention, the following specific compound within the scope of formula I may be mentioned: ((R)-3-amino-2-hydroxy-propyl)-cyclohexylmethyl-phosphinic acid benzyl ester or a pharmaceutically acceptable salt, hydrate or solvate thereof.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein especially by way of specific examples.

More specifically, the starting material, compound 1 is a known compound and can be synthesized by any of the procedures reported in the literature. For example, its synthesis is reported in U.S. Pat. No. 5,300,679 as well as in the articles of Froestl et al., J. Med. Chem. 1995, 38, 3297-3312, and Froestl et al., J. Med. Chem. 1995, 38, 3313-3331; all of which are incorporated herein by reference in their entirety. The compounds of formula IA or formula IB as disclosed herein can also be synthesized according to the following procedures of Scheme 1, wherein the R, $R_1$ and $R_2$ are as defined for Formula I unless otherwise indicated. It should be understood that various compounds encompassed within the scope of formula I can be synthesized following the procedures of Scheme 1 and employing suitable starting materials.

Scheme 1 illustrates a method for the preparation of the compounds of this invention. Again, various modifications can be made using other procedures known in the art which is readily appreciated by one skilled in the art. In step 1, Scheme 1, the amino group of compound 1 is suitably protected using any of the known amino protecting groups to form compound 2, wherein Pg is a suitable amino protecting group. For instance, the amino group of compound 1 is protected by tert-butyloxycarbonyl (Boc) by reacting with di-tert-butyldicarbonate (Boc$_2$O) in the presence of a suitable base such as potassium carbonate to afford amino-protected compound 2. This reaction is generally carried out at ambient reaction temperatures in a suitable organic solvent or a mixture of solvents, such as THF and water. Various other amino functional groups can similarly be employed in this reaction. See for example T. W. Greene, Protective Groups in Organic Synthesis, J. Wiley-Interscience Publication (1991).

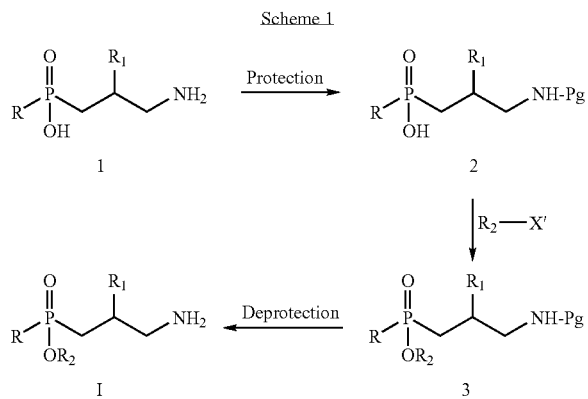

Scheme 1

In step 2, Scheme 1, the amino protected compound 2 is reacted with a suitable derivative of ester forming compound such as R$_2$—X', wherein X' is halogen or a suitable leaving group such as sulfonate, for example, methanesulfonate (mesylate), trifluoromethanesulfonate (triflate) or p-toluenesulfonate (tosylate) or the like, or carboxylate such as acetate. This reaction is generally carried out in a suitable inert organic solvent such as toluene but any other solvent that is suitable to carry out this reaction can also be used including mixtures of solvents. Additionally, the reaction is generally carried out at sub-ambient, ambient or super-ambient temperatures. Normally, super-ambient temperatures are preferred as it increases the reaction rate.

In step 3, Scheme 1, compound 3 is subjected to suitable reaction conditions in order to deprotect the amino function. Generally, such deprotection reactions are carried out at sub-ambient temperatures, e.g., at about 0° C. in the presence of an acid such as hydrochloric acid in a suitable organic solvent such as ethyl acetate to afford compound I as amine hydrochloride.

In another aspect of this embodiment, a specific disease, a disorder or a condition that can be treated with the compound of formula I of this invention include, without any limitation: depression, bipolar disorders, anxiety disorders, psychiatric symptoms, cognitive impairment or memory disorders, schizophrenia, neuropathic pain and fibromyalgia. Again, in this embodiment of the invention the compound of formula I as described hereinabove includes enantiomers, stereoisomers, and tautomers of said compound and pharmaceutically acceptable salts, solvates or derivatives thereof, optionally in combination with one or more pharmaceutically acceptable carriers, diluents or excipients. Various embodiments of the compound of formula I as described hereinabove can be employed in this method of the invention.

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of γ-aminobutyric acid (GABA). That is, the active metabolite of the compounds of the present invention is a GABA$_B$ antagonist and thus compounds of this invention may be effectively administered to ameliorate any disease state which is mediated all or in part by the GABA$_B$ antagonist.

In one of the preferred embodiments of this invention the compounds of this invention are particularly suitable for treating depression. Various types of depressive disorders that can be treated by the compounds of this invention include without any limitation are the following: major depressive episode, dysthymia, melancholia, seasonal affective disorders and depression arising from pre-menstrual tension and adolescence.

A feature of depression or depressive disorders ("unipolar depression") is one or more major depressive episodes without a history of manic, mixed, or hypomanic episodes. See, Diagnostic and Statistical Manual of Mental Disorders, 4$^{th}$ Ed., ("DSM-IV") American Psychiatric Association, 1995, incorporated herein by reference. Each of the sub-classes of depressive disorders is differentiated by symptoms exhibited by a patient. For instance, a major depressive disorder is characterized by one or more major depressive episodes (i.e., at least two weeks of depressed mood or loss of interest accompanied by at least four additional symptoms of depression). Whereas dysthymia or dysthymic disorder is characterized by at least two years of depressed mood for more days than not, accompanied by additional depressive symptoms that do not meet criteria for a major depressive episode. Thus, dysthymic disorder and major depressive disorder are differentiated based on severity, chronicity, and persistence. In major depressive disorder, the depressive mood must be present for most of the day, nearly every day, for a period of at least two weeks, whereas dysthymic disorder must be present for more days than not over a period of at least two years.

A melancholic feature is loss of interest or pleasure in all, or almost all, activities or a lack of reactivity to usually pleasurable stimuli. The individual's depressed mood does not improve, even temporarily, when something good happens. In addition, at least three of the following symptoms are present: a distinct quality of the depressed mood, depression that is regularly worst in the morning, early morning awakening, psychomotor retardation or agitation, significant anorexia or weight loss, or excessive or inappropriate guilt.

A feature of the seasonal affective disorders is the onset and remission of major depressive episodes at characteristic times of the year. In most cases, the episodes begin in fall or winter and remit in spring. Less commonly, there may be recurrent summer depressive episodes. See, DSM-IV or E. M. Tam et al., Can. J. Psychiatry 1995, 40, 457-466.

Bipolar disorders are further classified into four sub-categories: bipolar I disorder, bipolar II disorder, cyclothymic disorder and bipolar disorder not otherwise specified. Generally, bipolar disorders involve the presence (or history) of manic episodes, mixed episodes, or hypomanic episodes, usually accompanied by the presence (or history) of major depressive episodes. Bipolar I disorder is characterized by one or more manic or mixed episodes, usually accompanied by major depressive episodes. Bipolar II disorder is characterized by one or more major depressive episodes accompanied by at least one hypomanic episode. Cyclothymic disorder is characterized by at least two years of numerous periods of hypomanic symptoms that do not meet criteria for a manic episode and numerous periods of depressive symptoms that do not meet criteria for a major depressive episode.

In another aspect of this invention, the compounds of this invention are particularly useful in the treatment of a variety of anxiety disorders. Various types of anxiety disorders that can be treated without any limitation include the following: panic attack, social phobia, obsessive compulsive disorder, posttraumatic stress disorder and generalized anxiety disorder.

A panic attack or a panic disorder is a discrete period in which there is the sudden onset of intense apprehension, fearfulness, or terror, often associated with feelings of impending doom. During these attacks, symptoms such as shortness of breath, palpitations, chest pain or discomfort, choking or smothering sensations, and fear of "going crazy" or losing control are present.

Social phobia or social anxiety disorder is characterized by clinically significant anxiety provoked by exposure to certain types of social performance situations, often leading to avoidance behavior.

Obsessive compulsive disorder is characterized by obsessions (which cause marked anxiety or distress) and/or by compulsions (which serve to neutralize anxiety).

Posttraumatic stress disorder is characterized by the reexperiencing of an extremely traumatic event accompanied by symptoms of increased arousal and by avoidance of stimuli associated with the trauma.

Generalized anxiety disorder is characterized by at least six months of persistent and excessive anxiety and worry.

In a further aspect of the method of this invention, the compounds of formula I are particularly useful in treating psychiatric symptoms. Various psychiatric symptoms that can be treated by the compounds of this invention include without any limitation the following: anger, rejection sensitivity and lack of mental or physical energy.

In a further aspect of this embodiment of the invention, the compounds of this invention can also be used to treat psychiatric symptoms that are associated with premenstrual disorders. Specific psychiatric symptoms associated with menstrual disorders are selected from the group consisting of: anger, rejection sensitivity and lack of mental or physical energy.

Cognitive impairment or memory disorders is characterized by "memory loss", i.e., any disruption related to learning and memory. A "disruption relating to learning and memory" refers to any impairment associated with memory formation and/or memory recall. "Memory" can be, for example, short-term memory, long-term memory, explicit memory, i.e., memory for a conscious fact, e.g., the memory of a specific, event, or implicit or procedural memory, i.e., memory relating to an "unconsciously" performed task, e.g., riding a bicycle.

"Schizophrenia" is a disturbance that lasts for at least six months and includes at least one month of active-phase symptoms. That is, two or more of the following: delusions, hallucinations, disorganized speech, grossly disorganized speech, grossly disorganized or catatonic behavior and negative symptoms. The compounds of this invention can also be used to treat a variety of subtypes of schizophrenia. Various subtypes of schizophrenia and their definitions are set forth below.

Schizophreniform disorder is characterized by a symptomatic presentation that is equivalent to schizophrenia except for its duration (i.e., the disturbance lasts from one to six months) and the absence of a requirement that there be a decline in functioning.

Schizoaffective disorder is a disturbance in which a mood episode and the active-phase symptoms of schizophrenia occur together and were preceded or are followed by at least two weeks of delusions or hallucinations without prominent mood symptoms.

Delusional disorder is characterized by at least one month of nonbizarre delusions without other active-phase symptoms of schizophrenia.

Brief psychotic disorder is a psychotic disturbance that lasts more than one day and remits by one month.

Shared psychotic disorder is a disturbance that develops in an individual who is influenced by someone else who has an established delusion with similar content.

In psychotic disorder due to a general medical condition, the psychotic symptoms are judged to be a direct physiological consequence of a general medical condition.

In substance-induced psychotic disorder, the psychotic symptoms are judged to be a direct physiological consequence of a drug of abuse, a medication, or toxin exposure.

As used herein the term "Neuropathic pain" refers to a condition of pain associated with a nerve injury. Depending on the particular syndrome, the pain may be due to alterations of the brain or spinal cord or may be due to abnormalities in the nerve itself. Neuropathic pain may be idiopathic or induced by any causes including diseases (for example, amyloidosis, alcoholism, HIV, syphilis, virus, autoimmune disorder, cancer, porphyria, arachnoiditis, post herpetic neuralgia, Guillain-Barre syndrome, and diabetes, including Type I and Type II diabetes), chemicals (for example, toxins, lead, dapsone, vitamins, paclitaxel chemotherapy, and HAART therapy) and physical injuries to a particular nerve or nerve plexus (for example, trauma, compression, and constriction).

The inventive method is particularly useful for treating peripheral neuropathy and neuropathic pain such as peripheral neuropathy or neuropathic pain induced by HUV, chemicals (for example, toxins, lead, dapsone, vitamins, paclitaxel chemotherapy, HAART therapy), or diabetes such as type 1 and type 2 diabetes.

There are many ways to show that the compounds of the present invention are useful in treating various diseases as described herein, such as in animal models. See for example, "Animal Models as Simulations of Depression" by Paul Willner, *TiPS* 12:131-136 (April 1991); "Animal Models of Depression: An overview" by Paul Willner, *Pharmac. Ther.* 45:425-455 (1990), both of which are incorporated herein by reference. One such model to show efficacy of the compounds of this invention in treating depression is the chronic mild stress model of depression ("CMS").

CMS uses mild stressors, such as food and water deprivation, cage tilts, changes of cage mates, etc. Over a period of weeks of exposure to the mild stressors, the animals gradually reduce their consumption of a highly preferred sucrose solution which persists (in untreated animals) for several weeks following the cessation of stress. This decreased sensitivity to reward (the sucrose solution) reflects anhedonia, a symptom of a major depressive episode (see for example, Behavioral Pharmacol. 5: Suppl. 1, p. 86 (1994) where lithium, carbamazepine and ketoconazole were evaluated in CMS; Psychopharmacology 93:358-364 (1987) where a tricyclic antidepressant was evaluated in CMS; Behavioral Pharmacology: 5:344-350 (1994) where a catechol-O-methyl transferase inhibitor was evaluated in CMS).

Similarly, suitable other in vivo animal models that can be used to show the efficacy of the compounds of this invention in treating depression include forced swim test and/or social conflict test. The latter test can also be used to show the efficacy of the compounds of this invention in treating certain anxiety disorders. Another animal model to show the efficacy of the compounds of this invention in treating anxiety disorder is a social phobia test.

Object recognition test is another commonly used animal model to test the efficacy of the compounds in treating diseases involving various cognition impairment. See, for example Ennaceur et al., Behav. Brain Res., 1988, 31, 47-59. The test is based on the spontaneous exploratory activity of the animal and has the characteristics of episodic memory in humans. This memory test is sensitive to aging (Scali et al., Eur. J. Pharmacol., 1997, 325, 173-180) and to cholinergic dysfunctions (Bartolini et al., Pharm. Biochem. Behav. 1996, 53(2), 277-283) and is based on the differences in the exploration of two objects of fairly similar shape—one familiar, the other new.

Of course, clinical trials on humans may also be used to show the usefulness of the compounds of the present invention in treating depression such as using the abbreviated Hamilton Psychiatric Rating Scale for depression. This comprises a series of 17 categories in which the individual is rated, e.g., for depressed mood, guilt, suicide tendencies, insomnia, anxiety, etc., to reach a score which indicates to the clinician whether or not the patient is suffering depression.

Finally, various preferred embodiments of compounds of formula I and/or IB as described herein can be used in treating various diseases as discussed herein. That is, various preferred embodiments including specific compounds as described hereinabove can be used in the method of this invention.

In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route. More preferably, the compounds of this invention are administered by an oral route.

Finally, in yet another embodiment of this invention, there is also provided a pharmaceutical composition comprising a pharmaceutically acceptable carrier and a compound, including enantiomers, stereoisomers, and tautomers of said compound and pharmaceutically acceptable salts, solvates or derivatives thereof, with said compound having the general structure shown in formula I as described hereinabove. Again, various embodiments of the compound of formula I as described hereinabove can be employed in this composition of the invention.

As described herein, the pharmaceutical compositions of this invention feature $GABA_B$ antagonist activity and thus are useful in treating any disease, condition or a disorder caused due to the effects of $GABA_B$ in a patient. Again, as described above, all of the preferred embodiments of the compounds of this invention as disclosed hereinabove can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

Reactions generally are run under a nitrogen atmosphere. Solvents are dried over magnesium sulfate and are evaporated under vacuum on a rotary evaporator. TLC analyses are performed with EM Science silica gel 60 F254 plates with visualization by UV irradiation. Flash chromatography is performed using Alltech prepacked silica gel cartridges. The $^1$H NMR spectra are run at 300 MHz on a Gemini 300 or Varian VXR 300 spectrometer and are determined in a deuterated solvent, such as DMSO-$D_6$ or $CDCl_3$ unless otherwise noted. Chemical shifts values are indicated in parts per million (ppm) with reference to tetramethylsilane (TMS) as the internal standard. The LC/MS are run on a Micromass Platform LCZ.

As used in the examples and preparations that follow, the terms used therein shall have the meanings indicated: "kg" refers to kilograms, "g" refers to grams, "mg" refers to milligrams, "μg" refers to micrograms, "pg" refers to picograms, "lb" refers to pounds, "oz" refers to ounces, "mol" refers to moles, "mmol" refers to millimoles, "μmole" refers to micromoles, "nmole" refers to nanomoles, "L" refers to liters, "mL" or "ml" refers to milliliters, "μL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "THF" refers to tetrahydrofuran, "DMF" refers to dimethylformamide, "NMP" refers to 1-methyl-2-pyrrolidinone, "brine" refers to a saturated aqueous sodium chloride solution, "M" refers to molar, "mM" refers to millimolar, "μM" refers to micromolar, "nM" refers to nanomolar, "N" refers to normal, "TLC" refers to thin layer chromatography, "HPLC" refers to high performance liquid chromatography, "HRMS" refers to high resolution mass spectrum, "L.O.D." refers to loss on drying, "μCi" refers to microcuries, "i.p." refers to intraperitoneally, "i.v." refers to intravenously, anhyd=anhydrous; aq=aqueous; min=minute; hr=hour; d=day; sat.=saturated; s=singlet, d=doublet; t=triplet; q=quartet; m=multiplet; dd=doublet of doublets; br=broad; LC=liquid chromatograph; MS=mass spectrograph; ESI/MS=electrospray ionization/mass spectrograph; RT=retention time; M=molecular ion.

The following examples describe the procedures used for the preparation of various starting materials employed in the preparation of the compounds of this invention.

Example 1

((R)-3-Amino-2-hydroxy-propyl)-cyclohexylmethyl-phosphinic acid 3-oxo-1,3-dihydro-isobenzofuran-1-yl ester hydrochloride

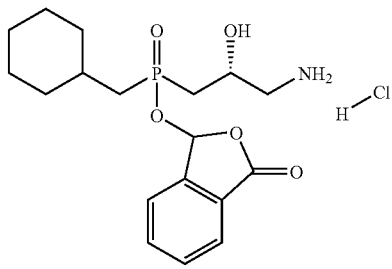

Step 1: ((R)-3-tert-Butoxycarbonylamino-2-hydroxy-propyl)-cyclohexylmethyl-phosphinic acid: ((R)-3-Amino-2-hydroxy-propyl)-cyclohexylmethyl-phosphinic acid (20.2 g, 86 mmol) was dissolved in an aqueous solution of potassium carbonate (35.6 g, 258 mmol in 270 mL of water), and stirred at room temperature during the slow addition of a solution of di-t-butyl-dicarbonate (24.36 g, 112 mmol) in THF (90 mL). The reaction mixture was left at room temperature for 4 hours, after which ethyl acetate (200 mL) was added. The aqueous phase was separated and washed with a second portion of ethyl acetate (200 mL), before carefully acidifying with 1N HCl (~450 mL) to pH2. Extraction into ethyl acetate (500 mL total), and drying ($MgSO_4$) gave a clear, colorless solution. Product began to crystallize from this solution upon standing. The total volume was reduced to ~150 mL (in vacuo) before adding heptane (300 mL). The solution was left at room temperature for 30 minutes to cool & crystallize. The solid product was filtered off, washed with 30% ethyl acetate/heptane (2×100 mL), and dried under high vacuum. ((R)-3-tert-butoxycarbonylamino-2-hydroxy-propyl)-cyclohexylmethyl-phosphinic acid (26.54 g, 92%) was isolated as colorless needles. 1H-NMR ($CDCl_3$, 300 MHz): δ 4.75 (s, H), 4.18 (br s, H), 3.4-3.24 (m, H), 3.21-3.09 (m, H), 2.01-1.58 (m, 10H), 1.43 (s, 9H), 1.37-0.95 (m, 6H). LC/MS m/z: $[M+H]^+$=336.4.

Step 2: ((R)-3-tert-Butoxycarbonylamino-2-hydroxy-propyl)-cyclohexylmethyl-phosphinic acid 3-oxo-1,3-dihydro-isobenzofuran-1-yl ester: To a solution of ((R)-3-tert-butoxycarbonylamino-2-hydroxy-propyl)-cyclohexylmethyl-phosphinic acid (0.5 g, 1.49 mmol) in 30 mL toluene was added 3-bromo-3H-isobenzofuran-1-one (952 mg, 4.47 mmol) and silver carbonate (1.23 g, 4.47 mmol). The reaction mixture was heated to 120° C. for 2 h. After filtering hot and concentrating in vacuo the crude product was purified by gradient flash chromatography (methanol/methylene chloride) on a 35 g RediSep disposable column to give ((R)-3-tert-butoxycarbonylamino-2-hydroxy-propyl)-cyclohexylmethyl-phosphinic acid 3-oxo-1,3-dihydro-isobenzofuran-1-yl ester (150 mg, 0.32 mmol). $^1$H NMR ($CDCl_3$, 300 MHz): δ 7.92 (m, 1H), 7.73 (m, 2H), 7.12 (m, 1H), 5.1 (m, 1H), 4.40 (m, 1H), 4.2 (m, 1H), 3.4-3.22 (m, 1H), 3.20-3.04 (m, 1H), 2.01-1.58 (m, 10H), 1.48 (s, 9H), 1.40-0.95 (m, 6H). LC/MS m/z: $[M+H]^+$=468.

Step 3: ((R)-3-Amino-2-hydroxy-propyl)-cyclohexylmethyl-phosphinic acid 3-oxo-1,3-dihydro-isobenzofuran-1-yl ester hydrochloride: To a solution of ((R)-3-tert-butoxycarbonylamino-2-hydroxy-propyl)-cyclohexylmethyl-phosphinic acid 3-oxo-1,3-dihydro-isobenzofuran-1-yl ester (140 mg, 0.3 mmol) in 2 mL dioxane was added a 4N HCl/dioxane solution (5.0 mL, 20 mmol). After 2 h the reaction mixture was concentrated in vacuo and the resulting residue taken up in ethyl acetate and was concentrated in vacuo to yield ((R)-3-amino-2-hydroxy-propyl)-cyclohexylmethyl-phosphinic acid 3-oxo-1,3-dihydro-isobenzofuran-1-yl ester hydrochloride (120 mg, 0.3 mmol). $^1$H NMR ($CD_3OD$, 300 MHz): δ 7.92 (m, 1H), 7.73 (m, 2H), 7.15 (m, 1H), 4.40 (m, 1H), 3.4-3.22 (m, 1H), 3.20-3.04 (m, 1H), 2.01-1.8 (m, 6H), 1.75-1.60 (m, 4H), 1.50-1.0 (m, 7H). $^{31}$P NMR ($CD_3OD$, 300 MHz): δ 61.4, 60.6. LC/MS m/z: $[M+H]^+$=368

Example 2

2,2-Dimethyl-propionic acid ((R)-3-amino-2-hydroxy-propyl)-cyclohexylmethyl-phosphinoyloxymethyl ester

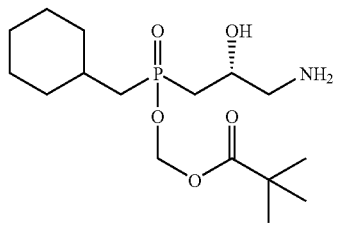

Step 1: ((R)-3-Benzyloxycarbonylamino-2-hydroxy-propyl)-cyclohexylmethyl-phosphinic acid: To a mixture of ((R)-3-amino-2-hydroxy-propyl)-cyclohexylmethyl-phosphinic acid (7.05 g, 30 mmol) and potassium carbonate (12.42 g, 90 mmol) in water (90 mL) and THF (30 mL) was added benzyl chloroformate (7.65 g, 45 mmol). After stirring for 3 h at room temperature, the reaction mixture was diluted with ethyl acetate (150 mL) and 2N HCl (90 mL). After stirring vigorously for 10 min the aqueous layer was removed and the organic layer was diluted with heptane (200 mL). The resulting white precipitate was collected to yield ((R)-3-benzyloxycarbonylamino-2-hydroxy-propyl)-cyclohexylmethyl-phosphinic acid (10.5 g, 28 mmol). $^1$H NMR (CDCl$_3$, 300 MHz): δ 7.32 (m, 5H), 5.45 (br s, 1H), 5.10 (s, 2H), 4.2 (m, 1H), 3.4 (dd, 1H), 3.20 (dd, 1H), 2.01-1.55 (m, 10H), 1.40-0.95 (m, 5H). $^{31}$P NMR (CDCl$_3$, 300 MHz): δ 57.3. LC/MS m/z: [M+H]$^+$=370.

Step 2: 2,2-Dimethyl-propionic acid ((R)-3-benzyloxycarbonylamino-2-hydroxy-propyl)-cyclohexylmethyl-phosphinoyloxymethyl ester: To a solution of ((R)-3-benzyloxycarbonylamino-2-hydroxy-propyl)-cyclohexylmethyl-phosphinic acid (1.0 g, 2.71 mmol) and chloromethyl pivalate (407 mg, 2.71 mmol) in chloroform (50 mL) at 60° C. was added silver oxide (754 mg, 3.25 mmol). After 3 h the reaction mixture was concentrated in vacuo and the residue taken up in ether (20 mL) and filtered through celite. The organic layer was diluted with ethyl acetate (100 mL) and was washed with 1N HCl (15 mL), saturated sodium bicarbonate solution (15 mL) and brine (20 mL). The organic was dried over magnesium sulfate, filtered and concentrated in vacuo to give the crude product. Purification by gradient flash chromatography (methanol/methylene chloride) on a 35 g RediSep disposable column gave 2,2-dimethyl-propionic acid ((R)-3-benzyloxycarbonylamino-2-hydroxy-propyl)-cyclohexylmethyl-phosphinoyloxymethyl ester (190 mg, 0.39 mmol). $^1$H NMR (CDCl$_3$, 300 MHz): δ 7.32 (m, 5H), 5.65 (m, 1H), 5.10 (s, 2H), 4.2 (m, 1H), 3.4 (m, 1H), 3.20 (m, 1H), 2.01-1.55 (m, 14H), 1.40-0.95 (m, 11H). $^{31}$P NMR (CDCl$_3$, 300 MHz): δ 57.3. LC/MS nm/z: [M+H]$^+$=484.

Step 3: 2,2-Dimethyl-propionic acid ((R)-3-amino-2-hydroxy-propyl)-cyclohexylmethyl-phosphinoyloxymethyl ester: 2,2-Dimethyl-propionic acid ((R)-3-benzyloxycarbonylamino-2-hydroxy-propyl)-cyclohexylmethyl-phosphinoyloxymethyl ester (0.90 g, 0.39 mmol) was dissolved in ethanol (35 mL) and was hydrogenated via a hydrogen par shaker for 3 h at 50 psi with 10% Pd/C (0.09 g) as a catalyst. The reaction was filtered through celite and concentrated in vacuo to give 2,2-dimethyl-propionic acid ((R)-3-amino-2-hydroxy-propyl)-cyclohexylmethyl-phosphinoyloxymethyl ester (130 mg, 0.37 mmol). $^1$H NMR (CDCl$_3$, 300 MHz): δ 5.65 (m, 1H), 4.2 (m, 1H), 3.8 (m, 1H), 3.60 (m, 1H), 2.01-1.55 (m, 14H), 1.40-0.95 (m, 11H). $^{31}$P NMR (CDCl$_3$, 300 MHz): δ 60.65, 59.20. LC/MS m/z: [M+H]$^+$=350.

Example 3

((R)-3-Amino-2-hydroxy-propyl)-cyclohexylmethyl-phosphinic acid ethoxycarbonyloxymethyl ester

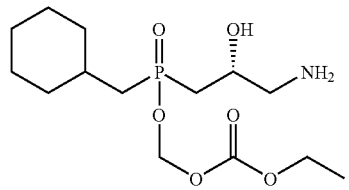

Step 1: (3-Benzyloxycarbonylamino-2-hydroxy-propyl)-cyclohexylmethyl-phospinic acid ethoxycarbonyloxymethyl ester: To a solution of ((R)-3-benzyloxycarbonylamino-2-hydroxy-propyl)-cyclohexylmethyl-phosphinic acid (1.0 g, 2.71 mmol) and carbonic acid chloromethyl ester ethyl ester (1.13 g, 8.16 mmol) in toluene (60 mL) was added silver carbonate (2.26 g, 8.16 mmol). The reaction mixture was heated at reflux for 3 h. The reaction mixture was then filtered and was concentrated in vacuo. Purification by gradient flash chromatography (methanol/methylene chloride) on a 35 g RediSep disposable column gave (3-benzyloxycarbonylamino-2-hydroxy-propyl)-cyclohexylmethyl-phosphinic acid ethoxycarbonyloxymethyl ester (300 mg, 0.63 mmol). $^1$H-NMR (CDCl$_3$, 300 MHz): δ 7.35 (m, 5H), 5.65 (m, 2H), 5.45 (br s, 1H), 5.10 (s, 2H), 4.2 (m, 2H), 3.45 (dd, 1H), 3.20 (dd, 1H), 2.01-1.55 (m, 11H), 1.40-0.95 (m, 8H).

Carbonic acid chloromethyl ester ethyl ester as used hereinabove is prepared in accordance of the procedures as set forth in Boehme, Horst; Budde, Juergen; "Chloromethyl, Mercaptomethyl, and Imidomethyl Carbonates" Synthesis, 1971, (11), 588-90.

Step 2: ((R)-3-Amino-2-hydroxy-propyl)-cyclohexylmethyl-phosphinic acid ethoxycarbonyloxymethyl ester: (3-Benzyloxycarbonylamino-2-hydroxy-propyl)-cyclohexylmethyl-phosphinic acid ethoxycarbonyloxymethyl ester (0.263 g, 0.56 mmol) was dissolved in absolute ethanol (28 mL) and hydrogenated at RT via a hydrogen Paar shaker for 1 h at 55 psi with 10% Pd/C (0.127 g). The reaction mixture was filtered through celite and concentrated in vacuo to yield the title compound (187 mg, 0.56 mmol) as a foamy white solid. $^1$H NMR (CDCl$_3$, 300 MHz): δ 7.90 (bs, 2H), 5.69 (m, 2H), 4.51 (bs, 1H), 4.23 (q, 2H), 3.27 (m, 1H), 3.17 (m, 1H), 2.20 (m, 2H), 1.88-1.64 (m, 8H), 1.34-1.00 (m, 6H), 1.32 (t, 3H). $^{31}$P NMR (CDCl$_3$, 300 MHz): δ 61.14, 59.63. LC/MS m/z: [M+H]$^+$=338.

Example 4

((R)-3-Amino-2-hydroxy-propyl)-cyclohexylmethyl-phosphinic acid phenyl ester hydrochloride

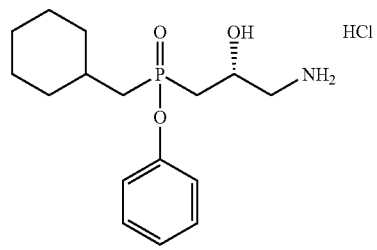

Step 1: ((R)-3-tert-Butoxycarbonylamino-2-hydroxy-propyl)-cyclohexylmethyl-phosphinic acid phenyl ester: To a solution of ((R)-3-tert-butoxycarbonylamino-2-hydroxy-propyl)-cyclohexylmethyl-phosphinic acid (0.67 g, 2.0 mmol) in 10 mL THF at 0° C. was added 1-chloro-N, N-2-trimethyl-1-propenylamine (319 mg, 2.4 mmol). After stirring for 10 min at 0° C., a solution of phenol (188 mg, 2.0 mmol) and triethylamine (243 mg, 2.4 mmol) in THF (3 mL) was added dropwise. After addition the reaction mixture was stirred at 0° C. for 2 h and then room temperature for 16 h. The reaction was diluted with ethyl acetate and washed with water and brine. The organic layer was dried with magnesium sulfate, filtered and concentrated in vacuo to give the crude product. Purification by gradient flash chromatography (methanol/methylene chloride) on a 35 g RediSep disposable column gave ((R)-3-tert-butoxycarbonylamino-2-hydroxy-propyl)-cyclohexylmethyl-phosphinic acid phenyl ester (500 mg, 1.22 mmol). $^1$H-NMR (CDCl$_3$, 300 MHz): δ 7.35 (m, 2H), 7.18 (m, 3H), 4.18 (br s, H), −33.21-3.09 (m, 2H), 2.01-1.58 (m, 10H), 1.43-0.95 (m, 15H). $^{31}$P NMR (CD$_3$OD, 300 MHz): δ 57.90, 58.65.

Step 2: ((R)-3-Amino-2-hydroxy-propyl)-cyclohexylmethyl-phosphinic acid phenyl ester hydrochloride: To a 0° C. solution of ((R)-3-tert-butoxycarbonylamino-2-hydroxy-propyl)-cyclohexylmethyl-phosphinic acid phenyl ester (495 mg, 1.2 mmol) in ethyl acetate (10 mL) was bubbled in HCl gas until saturated, via a pipette at a rate such that the temperature did not exceed 10° C. Once saturated, the reaction mixture was stirred at room temperature for 2 h and then concentrated in vacuo. The resulting residue was triturated with ether (100 mL) and the resulting solid collected to give ((R)-3-amino-2-hydroxy-propyl)-cyclohexylmethyl-phosphinic acid phenyl ester hydrochloride (248 mg, 0.71 mmol). $^1$H-NMR (CD$_3$OD, 300 MHz): δ 7.35 (m, 2H), 7.18 (m, 3H), 4.18 (br s, H), 3.21-3.09 (m, 2H), 2.01-1.58 (m, 10H), 1.43-0.95 (m, 9H). $^{31}$P NMR (CD$_3$OD, 300 MHz): δ 57.12, 57.47. LC/MS m/z: [M+H]$^+$=312.

Example 5

((R)-3-Amino-2-hydroxy-propyl)-cyclohexylmethyl-phosphinic acid benzyl ester hydrochloride

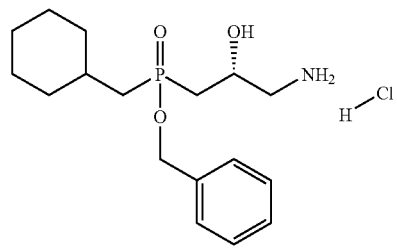

Step 1: ((R)-3-tert-Butoxycarbonylamino-2-hydroxy-propyl)-cyclohexylmethyl-phosphinic acid was prepared following the procedures as set forth in Step 1, Example 1.

Step 2: ((R)-3-tert-Butoxycarbonylamino-2-hydroxy-propyl)-cyclohexylmethyl-phosphinic acid benzyl ester: ((R)-3-tert-Butoxycarbonylamino-2-hydroxy-propyl)-cyclohexylmethyl-phosphinic acid (8.0 g, 23.8 mmol) was dissolved in a solution of potassium carbonate (3.30 g, 23.8 mmol) and water (33 mL) and stirred with gentle warming. The water was removed in vacuo and the residue dried under vacuum for 24 hours at 75° C. in the presence of phosphorous pentoxide to give the potassium salt as a white solid. To the potassium salt under a nitrogen atmosphere was added acetonitrile (200 mL), benzylbromide (4.08 g, 23.8 mmol) and 18-crown-6 (0.03 g, 0.120 mmol), and the mixture refluxed overnight at 80° C., with stirring. The reaction was cooled to room temperature, filtered and the filtrate concentrated in vacuo to give the crude product as a foam (10.2 g). The crude product was purified by gradient flash chromatography (25% ethyl acetate/methylene chloride to 100% ethyl acetate) to give the product as a white solid (6.43 g, 15.05 mmol). $^1$H NMR (CDCl$_3$, 300 MHz): δ 7.42-7.31 (m, 5H), 5.05 (t, 3H), 4.48-4.40 (m, 1H), 4.18-4.02 (m, 1H), 3.42-3.22 (m, 1H), 3.20-3.04 (m, 1H), 2.01-1.58 (m, 10H), 1.48 (s, 9H), 1.40-0.95 (m, 5H). LC/MS m/z: [M+H]$^+$=426.2.

Step 3: ((R)-3-Amino-2-hydroxy-propyl)-cyclohexylmethyl-phosphinic acid benzyl ester hydrochloride: ((R)-3-tert-Butoxycarbonylamino-2-hydroxy-propyl)-cyclohexylmethyl-phosphinic acid benzyl ester (300 mg, 0.7 mmol) was dissolved in ethyl acetate (7 mL) and cooled in an ice bath with stirring. HCl gas was bubbled into the solution, until saturated, via a pipette at a rate such that the temperature did not exceed 10° C. The reaction was stirred at 0° C. and the progress monitored by HPLC. Upon completion (3-4 hours) the reaction was concentrated in vacuo at room temperature and the residue placed under high vacuum for a few hours to give a sticky foam (215 mg, 0.6 mmol). $^1$H NMR (CDCl$_3$, 300 MHz): δ 8.26 (br S, 3H), 7.51-7.23 (m, 5H), 5.38-4.93 (br.m, 3H), 4.58 (br.s, 1H), 3.48-3.03 (m, 2H), 2.40-2.02 (m, 2H), 1.98-1.52 (m, 8H), 1.38-0.85 (m, 5H). LC/MS m/z: [M+H]$^+$=326.1.

Biological Examples

Example 6

This Example 6 demonstrates the improved and/or comparable bioavailability of the compounds of the present invention.

Animals: Male CD1 mice (Charles River) weighing about 25 g—with free access to food and water.

Dose Groups The compounds of this invention were administered to the test animals at a dose, which is molar equivalent to 10 mg/kg of the parent compound, ((R)-3-amino-2-hydroxy-propyl)-cyclohexylmethyl-phosphinic acid. Each of the test compounds was formulated at this dose level to yield a dose volume of 10 mL/kg and administered by oral gavage to a group of three mice per time point in each study group.

Formulations: The compounds of this invention were dissolved in vehicle of 0.2% Tween 80 and 0.5% methylcellulose (MC) at a concentration of about 1 mg/mL.

Samples: The blood samples (for plasma) were collected at the following time points: 5, 15 30 and 45 min predose; and 1, 2, 3, 4, 5, and 7 hrs post-dose. Brains were collected at 2, 4 and 7 hrs post-dose Blood Handling The blood samples were added to tubes containing 20 µL of a stock 10 mg/ml solution of sodium fluoride. The blood tubes were then stored in a refrigerator at approximately about 4° C. The volume of blood in each of these samples was about 0.4 mL. The samples were then centrifuged in a refrigerated centrifuge. The plasma samples were then stored in a freezer maintained at about −20° C.

Brain Handling The brains were removed following dissection of the animals at the specified time intervals and stored on dry ice and transferred to a freezer maintained at about −20° C. Each of the mouse brain was first homogenized with 3.0 mL of 25% acetonitrile before using for bioanalysis as described below.

Bioanalysis: All plasma and brain samples were then analyzed for concentrations of the test compound as well as the parent compound, ((R)-3-amino-2-hydroxy-propyl)-cyclohexylmethyl-phosphinic acid by LC/MS/MS. The relative amounts of parent compound, ((R)-3-amino-2-hydroxy-propyl)-cyclohexylmethyl-phosphinic acid, observed in the plasma for each of the test compounds of this invention are summarized in Table 1.

TABLE 1

| EXAMPLE NO. | Percent Relative Bioavailability of compound in plasma* |
|---|---|
| 2 | 101 |
| 5 | 122 |

*Relative to the bioavailability of the parent compound when dosed as itself.

The analyses of the brain samples by LC/MS/MS showed that the concentration of the parent compound in brain was proportional to the concentration of the parent compound in plasma. Whereas, in most cases, the levels of the test compound was too small to be detected for all of the test compounds analyzed.

Example 7

Porsolt's Forced Swim Test

The effects measured in this model have been correlated to antidepressant efficacy for drugs. The paradigm of this model is that an effective antidepressant compound will cause a rat to make greater attempts to escape a water-filled cylinder than a rat given vehicle only.

Animals used in this study are non-naive male Sprague Dawley rats weighing between 225-350 grams. The test apparatus consists of 6 clear PLEXIGLAS® cylinders 40 cm high x 19 cm wide. Cylinders are filled to 18 cm with 25° C. water. Each rat is placed in a cylinder for a 15 minute training session. Following either subchronic or acute dosing of either vehicle (0.5% methylcellulose) or compound, animals are brought back 24 hours later for a 5 minute test session. These test sessions are videotaped for later scoring.

Subchronic dosing consists of administering drug three times in the 24-hour period between training and testing. The drug is administered 24 hrs., 5 hrs., and 1 hr. prior to the test session. Acute dosing consists of administering the drug once, 1 hour prior to the test session. Scoring is done using a time-sampling computer program. Every five seconds, animals are rated as demonstrating one of three behaviors: immobility, mild swim, or climbing. These sampling scores are then converted into percentages of the test session.

Example 8

Social Conflict Test

The effects measured in this model have been correlated either to antidepressant efficacy and/or anxiety efficacy for drugs. This test provides complex measures for prediction of anxiolytic and anxiogenic activity of drugs in behaviorally different groups of animals.

Male albino random-bred mice, weighing 18-20 g are used in this study. They are housed singly in self cleaning cages or in groups of ten. The cages used for the individual housing are made of solid metal walls 13 cm high with wire mesh floors (8×17 cm), which are placed 3 cm above trays with wood shavings. This wire-mesh floor ensured that the isolates are not handled throughout the period of single housing. The mice kept in groups are housed in large standard plastic cages (26×42×15 cm) with floors covered with wood shavings. All mice are housed under room lighting (with lights on from 0600 hours to 1800 hours) and under temperature ranging from 22° C. to 24° C. Food and water are available ad libitum.

The mice are observed in transparent cages (20×30×20 cm) with wood shavings on the floor and tops covered with transparent covers with apertures for air. The observations are performed under moderate room lighting from 0800 hours to 1300 hours.

Social interaction tests are started after 3 weeks of isolation and involve one singly housed mouse paired with the same group housed mouse. The isolates are allowed 15 min adaptation in the observational cages before the group-housed partners are introduced; the interaction ends after 4 min. This procedure, which suppresses aggression in group-housed mice and reduces their social behavior, facilitates active social behavior in isolates. The observation cages are cleaned and their floors are covered with new wood shavings after each interaction.

All subjects undergo four social interaction tests at 1-week intervals. The isolates are given a particular dose of the compounds of this invention (usually at about 1 mg/kg) or vehicle in a randomized order, while the group-housed partners remained untreated. The group-housed mice served only to stimulate social behavior in the isolates. In the event that a group-housed 'stimulus' mouse attacks the isolated mouse, the pair is excluded from the experiment.

The behavior of animals during the interactions are recorded on videotape. The tapes are later analyzed by an observer with no knowledge of the drug treatment. The frequency, total duration and latency of a number of aggressive, defensive-escape (timid), social and locomotor activities are recorded. Changes in social interaction time and total activity are then determined by comparing the means of the test compound administered groups to the vehicle control groups.

The social activities include the social sniff—sniffing the partner's head, body, genitals or tail; climb—the mouse places its forepaws on the partner's back, mostly in the shoulder region, and usually sniffs this area at the same time; and follow—following the partner by quiet walking.

The aggressive activities include attack—a fierce lunging at the partner often associated with biting; threat—a sideways or an upright stance with head and forebody movements toward the partner, and trying to bite the partner (offensive sideways or upright posture); and tail rattle—rapid vibration of the tail.

The timid activities include defense—the mouse responds to the partner's social behavior by raising forepaws, hunching the back (defensive upright posture) or by some rotation of the body bringing the legs closest to the other animal off the ground (defensive sideways posture); escape—a rapid running or jumping away from the partner; and alert posture—a sudden interruption of all movements with eyes and ears being directed toward the partner.

Locomotor activities include walk—any walking across the cage that is not apparently related to the partner; and rear—the mouse stands only on his hind legs and usually sniffs air or walls at the same time.

Example 9

Chronic Mild Stress Model (CMS)

The following CMS study is performed using the parent compound, ((R)-3-amino-2-hydroxy-propyl)-cyclohexylmethyl-phosphinic acid, (hereafter "compound") in comparison to known anti-depressant compound imipramine.

Male Wistar rats are brought into the laboratory two months before the start of the experiment at which time they weighed approximately 300 grams. Except as described below, the animals are singly housed, with food and water freely available, and maintained on a 12 hour light/dark cycle (lights on at 8 AM) at a temperature of about 22° C.

The animals are first trained to consume a 1% sucrose solution; training consists of eight 1 hour baseline tests in which sucrose is presented, in the home cage, following 14 hours food and water deprivation; intake is measured by weighing pre-weighed bottles containing the sucrose solution at the end of the test. Subsequently, sucrose consumption is monitored, under similar conditions, at weekly intervals throughout the whole experiment.

On the basis of their sucrose intakes in the final baseline test, the animals are divided into two matched groups. One group of animals is subjected to a chronic mild stress procedure for a period of 9 consecutive weeks. Each week of stress regime consisted of: two periods of food or water deprivation (12 and 14 hour), two periods of 45 degree cage tilt (12 and 14 hour+), two periods of intermittent overnight illumination (lights on and off every 2 hours), two 14 hour periods of soiled cage (200 ml water in sawdust bedding), two 14 hour periods of paired housing, two 14 hour periods of low intensity stroboscopic illumination (150 flashes/min). Stressors are applied continuously throughout the day and night, and scheduled randomly. Control animals are housed in a separate room and have no contact with the stressed animals. They are deprived of food and water for the 14 hours preceding each sucrose test, but otherwise food and water are freely available in the home cage. On the basis of their sucrose intake scores following 3 weeks of stress, both stressed and control animals are each divided further into matched subgroups (n=8), and for subsequent five weeks they receive daily administrations of vehicle (1 ml/kg, intraperitoneally (ip)) imipramine (10 mg/kg, ip) or compound (3 and 30 mg/kg orally). All drug injections are in a volume of 1 ml/kg body weight. Drugs are administered at 10 AM and sucrose tests are carried out 24 hours following the last drug treatment. After five weeks, the treatments are terminated and after one week of withdrawal a final sucrose test is carried out. Stress is continued throughout the period of treatment and withdrawal.

Results are analyzed by multiple analysis of variance, followed by Fisher's LSD test for post hoc comparisons of means. The activity of compound at the tested dose level of 3 and 30 mg/kg is equal to that of imipramine.

Example 10

Object Recognition Test

The object recognition test is a memory test. It measures the ability of mice (and rats) to differentiate between known and unknown objects and is therefore suitable for the determination of the memory-improving action of the compounds according to the invention.

The test can generally be carried out as described in the literature. (Blokland et al. NeuroReport 1998, 9, 4205-4208; Ennaceur, A., Delacour, J., Behav. Brain Res. 1988, 31, 47-59; Ennaceur, A., Meliani, K., Psychopharmacology 1992, 109, 321-330; Prickaerts, et al. Eur. J. Pharmacol. 1997, 337, 125-136).

In a first passage, a mouse in an otherwise empty relatively large observation arena is confronted with two identical objects. The mouse will extensively examine, i.e. sniff and touch, both objects. In a second passage, after an interval of 24 hours, the mouse is again tested in the observation arena. One of the known objects is now replaced by a new, unknown object. When a mouse recognizes the known object, it will especially examine the unknown object. After 24 hours, a mouse, however, has normally forgotten which object it has already examined in the first passage, and will therefore inspect both objects equally intensively. The administration of a substance having learning- and memory-improving action will lead to a mouse recognizing the object already seen 24 hours beforehand, in the first passage, as known. It will examine the new, unknown object in greater detail than the already known one. This memory power is expressed in a discrimination index. A discrimination index of zero means that the mouse examines both objects, the old and the new one, for the same length of time; i.e. it has not recognized the old object and reacts to both objects as if they were both unknown and new. A discrimination index of greater than zero means that the mouse has inspected the new object for longer than the old one; i.e. the mouse has recognized the old object.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound, including enantiomers, stereoisomers, and tautomers of said compound and pharmaceutically acceptable salts thereof, with said compound having the general structure shown in formula I:

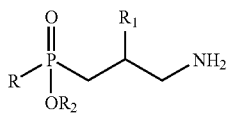

(I)

wherein:
R is $C_{1-8}$alkyl, $C_{3-8}$cycloalkyl$C_{1-4}$alkyl, aryl$C_{1-4}$alkyl or fluoroalkyl of the formula $C_nH_xF_y$ wherein n is an integer from 1 to 4, x is an integer from 0 to 8, y is an integer from 1 to 9 and sum of x and y is 2n+1;
$R_1$ is hydrogen or hydroxy;
$R_2$ is substituted or unsubstituted aryl, aryl$C_{1-4}$alkyl, heteroaryl or heteroarylalkyl, or CHWOCOX; wherein
  W is hydrogen or $C_{1-4}$alkyl;
  X is $C_{1-4}$alkyl, $C_{3-8}$cycloalkyl, aryl, heteroaryl, NHY or OY; and
  wherein
    Y is $C_{1-4}$alkyl, $C_{3-8}$cycloalkyl, aryl or heteroaryl.

2. The compound as set forth in claim 1, wherein
R is cyclopropylmethyl, cyclobutylmethyl, cyclopentylmethyl, cyclohexylmethyl, cycloheptylmethyl, cyclohexylethyl, cyclohexylpropyl, benzyl, and phenylethyl;
$R_1$ is hydroxy; $R_2$ is substituted or unsubstituted phenyl, benzyl or oxo-1,3-dihydroisobenzofuranyl, 5-methyl-[1,3]dioxol-2-one-methyl, gamma-butyrolacton-4-yl, or CHWOCOX; wherein
  W is hydrogen, methyl, ethyl, n-propyl or sec-butyl;
  X is methyl, ethyl, n-propyl, n-butyl, sec-butyl, tert-butyl, cyclohexyl or OY; and wherein
    Y is methyl, ethyl or n-propyl.

3. The compound as set forth in claim 1, wherein R is $C_{3-8}$cycloalkyl$C_{1-4}$alkyl and $R_1$ is hydroxy.

4. The compound as set forth in claim 1, wherein R is aryl$C_{1-4}$alkyl and $R_1$ is hydroxy.

5. The compound as set forth in claim 1, wherein R is $C_{5-7}$cycloalkyl$C_{1-4}$alkyl and $R_1$ is hydroxy.

6. The compound as set forth in claim 1, wherein R is phenyl$C_{1-4}$alkyl and $R_1$ is hydroxy.

7. The compound as set forth in claim 1, wherein said compound is of the formula IB:

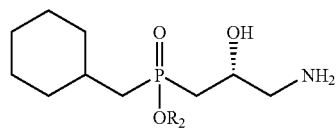

(IB)

wherein
$R_2$ is substituted or unsubstituted phenyl, benzyl, oxo-1,3-dihydroisobenzofuranyl or 5-methyl-[1,3]dioxol-2-one-methyl, or CHWOCOX; wherein
  W is hydrogen, methyl, ethyl, n-propyl or sec-butyl;
  X is methyl, ethyl, n-propyl, n-butyl, sec-butyl, tert-butyl, cyclohexyl or OY; and wherein
    Y is methyl, ethyl or n-propyl.

8. The compound as set forth in claim 1, which is selected from the group consisting of:
((R)-3-amino-2-hydroxy-propyl)-cyclohexylmethyl-phosphinic acid 3-oxo-1,3-dihydro-isobenzofuran-1-yl ester;
2,2-dimethyl-propionic acid ((R)-3-amino-2-hydroxy-propyl)-cyclohexylmethyl-phosphinoyloxymethyl ester;
((R)-3-amino-2-hydroxy-propyl)-cyclohexylmethyl-phosphinic acid ethoxycarbonyloxymethyl ester; and
((R)-3-amino-2-hydroxy-propyl)-cyclohexylmethyl-phosphinic acid phenyl ester;
((R)-3-amino-2-hydroxy-propyl)-cyclohexylmethyl-phosphinic acid benzyl ester;
(3-amino-2-hydroxy-propyl)-cyclohexylmethyl-phosphinic acid 5-methyl-2-oxo-[1,3]dioxol-4-ylmethyl ester; or
a pharmaceutically acceptable salt thereof.

9. The compound as set forth in claim 1, which is 2,2-dimethyl-propionic acid ((R)-3-amino-2-hydroxy-propyl)-cyclohexylmethyl-phosphinoyloxymethyl ester or a pharmaceutically acceptable salt thereof.

10. The compound as set forth in claim 1, which is ((R)-3-amino-2-hydroxy-propyl)-cyclohexylmethyl-phosphinic acid benzyl ester or a pharmaceutically acceptable salt thereof.

11. A pharmaceutical composition comprising one or more compounds of formula I, including enantiomers, stereoisomers, and tautomers of said compound and pharmaceutically acceptable salts, in combination with one or more pharmaceutically acceptable carriers, diluents or excipients:

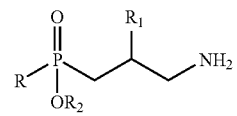

(I)

wherein:
R is $C_{1-8}$alkyl, $C_{3-8}$cycloalkyl$C_{1-4}$alkyl, arylC14alkyl or fluoroalkyl of the formula $C_nH_xF_y$, wherein n is an integer from 1 to 4, x is an integer from 0 to 8, y is an integer from i to 9 and sum of x and y is 2n+1;
$R_1$ is hydrogen or hydroxy;
$R_2$ is substituted or unsubstituted aryl, aryl$C_{1-4}$alkky1, heteroaryl or heteroarylalkyl, or CHWOCOX; wherein
  W is hydrogen or $C_{1-4}$alkyl;
  X is $C_{1-4}$alkyl, $C_{3-8}$cycloalkyl, aryl, heteroaryl, NHY or OY; and
  wherein
    Y is $C_{1-4}$alkyl, $C_{3-8}$cycloalkyl, aryl or heteroaryl.

12. The composition as set forth in claim 11, wherein said compound of formula I is having:
R is cyclopropylmethyl, cyclobutylmethyl, cyclopentylmethyl, cyclohexylmethyl, cycloheptylmethyl, cyclohexylethyl, cyclohexylpropyl, benzyl, and phenylethyl;
$R_1$ is hydroxy;
$R_2$ is substituted or unsubstituted phenyl, benzyl or oxo-1,3-dihydroisobenzofuranyl, 5-methyl-[1,3]dioxol-2-one-methyl, or CHWOCOX; wherein
  W is hydrogen, methyl, ethyl, n-propyl or sec-butyl;
  X is methyl, ethyl, n-propyl, n-butyl, sec-butyl, tert-butyl, cyclohexyl
    or OY; and wherein
    Y is methyl, ethyl or n-propyl.

13. The composition as set forth in claim 11, wherein said compound is selected from the group consisting of:
((R)-3-amino-2-hydroxy-propyl)-cyclohexylmethyl-phosphinic acid 3-oxo-1,3-dihydro-isobenzofuran-1-yl ester;

2,2-dimethyl-propionic acid ((R)-3-amino-2-hydroxy-propyl)-cyclohexylmethyl-phosphinoyloxymethyl ester;

((R)-3-amino-2-hydroxy-propyl)-cyclohexylmethyl-phosphinic acid ethoxycarbonyloxymethyl ester;

((R)-3-amino-2-hydroxy-propyl)-cyclohexylmethyl-phosphinic acid phenyl ester;

((R)-3-amino-2-hydroxy-propyl)-cyclohexylmethyl-phosphinic acid benzyl ester; and (3-amino-2-hydroxy-propyl)-cyclohexylmethyl-phosphinic acid 5-methyl-2-oxo-[1,3]dioxol-4-ylmethyl ester; or a pharmaceutically acceptable salt thereof.

\* \* \* \* \*